United States Patent [19]

Steenhuisen et al.

[11] Patent Number: 4,475,903
[45] Date of Patent: Oct. 9, 1984

[54] DISPOSABLE HYPODERMIC SYRINGE

[75] Inventors: Johannes E. Steenhuisen; Jan van Dijk, both of Olst, Netherlands

[73] Assignee: Duphar International Research B.V., Netherlands

[21] Appl. No.: 542,568

[22] Filed: Oct. 19, 1983

Related U.S. Application Data

[63] Continuation of Ser. No. 400,105, Jul. 20, 1982, abandoned.

[30] Foreign Application Priority Data

Jul. 23, 1981 [NL] Netherlands .................. 8103476

[51] Int. Cl.³ .............................................. A61M 5/00
[52] U.S. Cl. ........................... 604/111; 128/DIG. 18; 604/240
[58] Field of Search ............... 604/240, 241, 242, 243, 604/263, 192, 187, 188, 110, 111, 283, 199; 128/DIG. 18

[56] References Cited

U.S. PATENT DOCUMENTS

| | | | |
|---|---|---|---|
| 2,737,949 | 3/1956 | Brown | 604/243 |
| 2,750,719 | 6/1956 | Wandelt | 206/365 |
| 2,938,238 | 5/1960 | Gewecke et al. | 604/263 X |
| 3,074,541 | 1/1963 | Roehr | 206/364 |
| 3,203,545 | 8/1965 | Grossman | 206/364 |
| 3,209,752 | 10/1965 | Bujan et al. | 604/263 X |
| 3,270,743 | 9/1966 | Gingras | 604/199 |
| 3,485,239 | 12/1969 | Vanderbeck | 604/199 |
| 3,885,667 | 5/1975 | Spiegel et al. | 206/497 |
| 3,927,762 | 12/1975 | Zdarsky et al. | 206/497 |
| 3,989,045 | 11/1976 | Van Eck | 604/192 |
| 4,181,223 | 1/1980 | Millet | 206/365 |
| 4,194,509 | 3/1980 | Pickering et al. | 604/283 X |
| 4,300,678 | 11/1981 | Gyure et al. | 604/263 |

Primary Examiner—John D. Yasko
Attorney, Agent, or Firm—Stevens, Davis, Miller & Mosher

[57] ABSTRACT

The invention relates to a disposable syringe comprising a barrel which has on its front end a needle connection with injection needle and needle guard. The syringe is provided with a sealing member for the needle guard which consists of a sleeve of shrinkable plastic material. The sleeve is shrunk on one side around the needle connection and/or around the barrel or a front part of the barrel, and on the other side around a part of the needle guard adjoining the needle connection.

7 Claims, 4 Drawing Figures

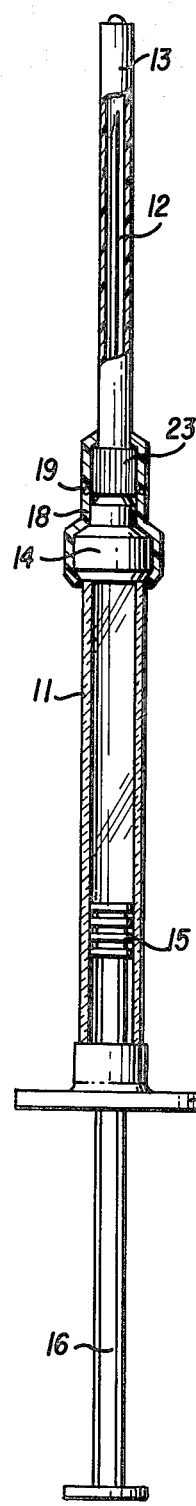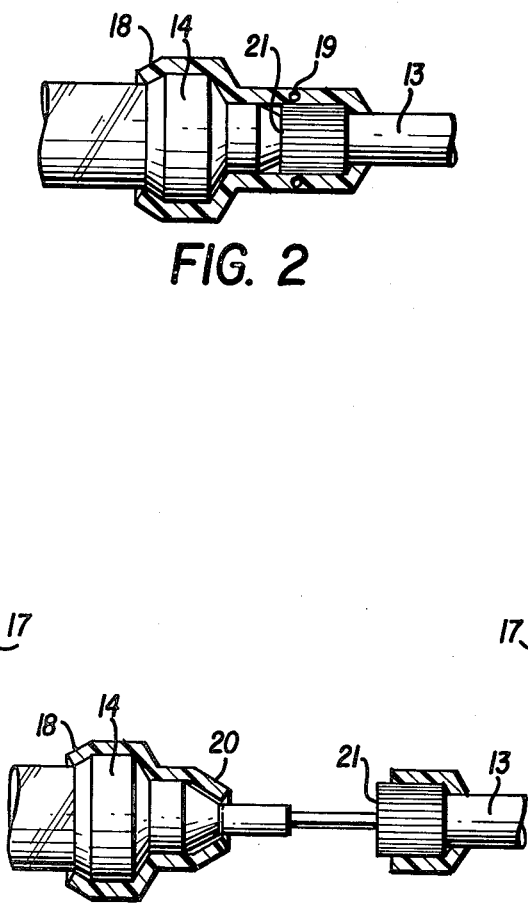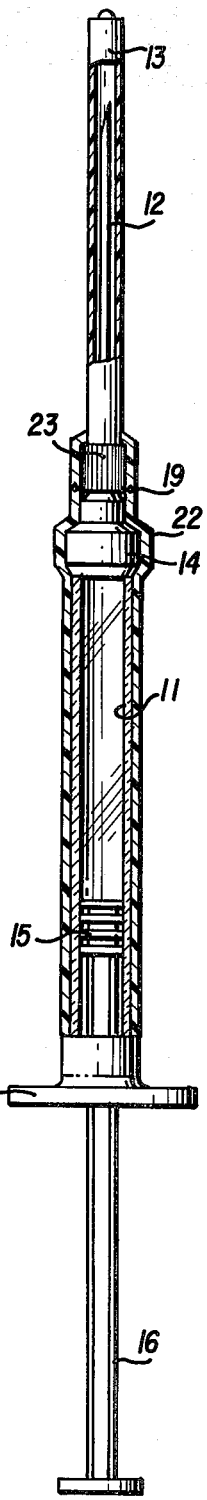
FIG. 1  FIG. 2  FIG. 3  FIG. 4

DISPOSABLE HYPODERMIC SYRINGE

This application is a continuation of application Ser. No. 400,105, filed 7/20/82.

BACKGROUND OF THE INVENTION

1. Field of the Invention

The present invention relates to a disposable syringe comprising a barrel which is open at each end and in which a piston which is movable in the barrel and seals same is or can be provided, to which piston a piston rod is or can be connected; in which the barrel on its front end is provided with a needle connection, and wherein an injection needle is attached; and in which a needle guard is provided over the injection needle, the open end of the guard being detachably connected to the needle connection on the front end of the barrel.

2. Discussion of the Prior Art

Such a syringe is disclosed in Netherlands Patent Application No. 7603511 in the name of Applicants. In the syringe described in said Patent Application the needle connection consists of a needle mount, and the open end of the needle guard is connected in a clamping manner to a part of the needle mount suitable for that purpose. Such a connection of the needle guard is more clearly shown in Netherlands Patent Application No. 7401607, also in the name of Applicants. The part of the needle mount remote from the injection needle is connected to the barrel, for example, by means of riveting or shrinking. At its other end the needle mount is usually narrowed to a sleeve-like part so that an injection needle can be connected in it. The needle guard provided over the injection needle usually has a thickened open end which is connected to the sleeve-like part of the needle mount in a clamping manner. As a result of this, a sterile sealing for the needle is obtained. Of course, the sterility of the injection needle is an essential condition for using the syringe.

The syringe known from the above-mentioned Netherlands Patent Application No. 7603511 has the disadvantage that the user can not satisfactorily control the sterility of the needle. Specifically the user cannot ascertain whether the needle guard has already been removed previously or, for example, has come loose during transport and has subsequently been replaced in its original position. In other words the user is not sure of the sterility of the injection needle.

In the above-mentioned Netherlands Patent Application No. 7401607 a safety member for an injection syringe is described which has as one of its objects the elimination of the above disadvantage. The safety member described in this Patent Application is a cap having a central bore which is slid around the needle guard up to the thickened end thereof, and which has breakable elements with which it is connected to the syringe in a detachable but irreversible manner. The user of the syringe can establish at a glance by means of said cap whether the needle guard has previously been removed.

The above-mentioned safety member gives excellent satisfaction in a syringe comprising an ampoule holder or cartridge holder; such a syringe is disclosed in the above Netherlands Patent Application No. 7401607. The plastic cap can simply be connected to the plastic cartridge holder in a few points, for example, by spot-welding. However, when such a cartridge holder, which is quite an expensive component for a disposable syringe, is lacking, as in the syringe described in the above-mentioned Netherlands Patent Application No. 7603511, the connection of the safety cap to the needle holder which usually is manufactured from aluminium is substantially impossible, in particular because high requirements have to be imposed upon this connection. In fact, on the one hand the connection elements between safety cap and needle mount must not come loose during storage and transport, but on the other hand it must be possible by a very simple operation, for example a simple rotating movement, to remove the safety member for use of the injection syringe. In addition to the disadvantage that the above-mentioned safety cap is hardly suitable for use in a syringe not having a cartridge holder, the cap has additional disadvantages. A disposable syringe should be cheap and hence of a simple construction. A safety cap as described above is a comparatively expensive solution to the problem in question. Another important disadvantage is the extra operation which has to be carried out to remove the cap for use of the syringe.

SUMMARY OF THE INVENTION

It is the object of the inventors to develop a safety member for a syringe which does not exhibit the above-mentioned disadvantages. For that purpose, they have developed a syringe of the kind mentioned in the opening paragraph which is characterized in that the injection needle has a sealing member for the needle guard which consists of a sleeve of shrinkable plastic sheet. This sleeve is shrunk on the one side around the needle connection and/or around the barrel or a front part of the barrel and, on the other side around a part of the needle guard adjoining the needle connection.

Such a sleeve of shrinkable sheet provides a cheap solution to the problem in question, because it provides an assurance that the needle guard has not been removed. The sleeve can easily be shrunk around the needle connection and needle guard irrespective of the material of which these components of the syringe are constructed. Moreover, no extra operation is necessary to break the seal because simultaneously with the removal of the needle guard, the sleeve detaches from the needle connection or needle guard or breaks apart. The remaining part of the sleeve, if any, shrunk around the needle guard is then removed simultaneously with the needle guard. The needle connection or the connection means for the needle comprises a needle mount as described in the above-mentioned Netherlands Patent Application No. 7603511, e.g. from metal or plastic material, or alternatively forms an integral part of the barrel and consequently is made from the same material as the barrel, preferably from glass. In the latter case the barrel in the area of the needle connection is narrowed to a sleeve-like part wherein the needle is attached, e.g. by luting.

Shrinkable sheet is now frequently used, in particular in the pharmaceutical and food industries, for example, for the so-called "tamper-proof" sealing of bottles. Examples of shrinkable capsules for bottles are to be found in U.S. Pat. No. 3,746,201 and German Patent Application No. 2,057,901. The capsules described in these Patent Publications comprise a pull-off lug and strip by means of which the capsule can be removed from the bottle. Such a pull-off lug would be less suitable for the sealing sleeve for the syringe of the application because again an extra operation would be necessary to remove the sleeve. Moreover, a pull-off lug for a sealing sleeve of a syringe would become too small for ready grasping;

as a matter of fact, the size of the sleeve, and hence the dimensions of the pull-off lug, should be adapted to the article to be sealed. U.S. Pat. No. 3,101,841 relates to a two-part package for an injection needle, namely a holder and a cap. The cap can be connected to the holder by heating the lower edge and then clamping it around the holder by an inwardly directed force. The disadvantage of the sterile packaging while heating of an injection needle is that the whole operation, including the local heating of the package parts to be connected together, would have to take place in a sterile room. In contrst, a needle guard in accordance with the present invention, for example, may be in the form of a sheath which can simply be slid onto the needle, and as such is an example of a very handy component of a disposable syringe which can be assembled in a sterile room.

The sleeve of shrinkable sheet utilized to seal the needle guard of the syringe according to the invention is made of a known synthetic resin sheet, for example, a monoaxially prestretched sheet of hard PVC.

In U.S. Pat. No. 3,485,239 an injection syringe provided with a gas permeable paper wrap sealably connecting the needle cap and the barrel is disclosed. The purpose of this paper wrap is different from that of the sealing member for the needle guard of the present invention. The paper wrap serves to secure the cap to the barrel in such a manner that the assembled unit can be sterilized. Therefore the band is of a special material allowing the entry of sterilizing gases during sterilization but maintaining the contents of the syringe after sterilization in a sterilized condition. In addition to the different material, this known sealing bond does not provide a good indication of breakage of the seal, such an indication be a prerequisite the sealing member for the needle guard of the present invention.

The sleeve is provided as follows. A sleeve of a suitable shrinkable sheet, having a diameter which is slightly larger than that of the components to be sealed, is slid on the front onto the desired portion of the syringe provided with a needle guard. The sleeve is then shrunk around the components to be sealed by heating, for example by means of hot air or infra-red radiation. The temperature at which the shrinkable sheet can shrink is usually above approximately 80° C. It is not desired to heat the syringe during shrinkage at too high a temperature for too long a period of time, because this may be detrimental to the medicament to be injected and because the stress in the barrel would become too great. It is therefore preferred during shrinking to use a temperature of approximately 90° C. and a shrinkage period which is as short as possible. In order to keep the shrinkage time as short as possible, the sealing is preferably carried out automatically.

A good indication of seal breakage is extraordinarily important. In fact, it is the object of the seal to provide an indication for the user whether the needle guard has already been removed. The location where the sleeve is shrunk around the components to be sealed is of great importance for a good indication of seal breakage. When an unperforated sleeve is used, it is preferably shrunk on the one side around the needle connection and/or around the barrel or a front part of the barrel and on the other side around a part of the needle guard in such a manner that one end of the sleeve forms a radially inwardly directed collar behind a thickened part of the needle connection or front part of the barrel, and that the other end forms a cylinder having a diameter which remains the same around the part of the needle guard adjoining the needle connection. When the needle guard is removed, the end of the sleeve which is shrunk around the open end of the needle guard will come loose from the needle guard, after which it will become substantially impossible to put the needle guard back again in its original location since the now open end of the sleeve remaining on the needle connection or front part of the barrel will in fact prevent the reconnection of the needle guard to the needle connection or front part of the barrel.

Although an unperforated sleeve can contribute to the maintenance of the sterility of the syringe, a sleeve of shrinkable sheet comprising a circumferential perforation is nevertheless to be preferred. When the needle guard is removed, the sleeve will break apart on said perforation. In contrast to an unperforated sleeve, the force which has to be applied to break the seal can be adjusted at will by adjusting the degree of perforation of the circumferential perforation in the sleeve. Furthermore, in an unperforated sleeve it is more difficult to combine a sufficiently rigid seal of the needle guard with a good indication of seal breakage. In a sleeve of shrinkable sheet having a circumferential perforation, the location of the perforation can be determined at will without this influencing the firmness of the seal of the needle guard. Finally, after breaking the seal, the sleeve does not form a obstruction for the use of the syringe, that is to say, when administering an injection. This use without obstruction is achieved with greater difficulty in an unperforated sleeve because the sleeve after removal of the needle guard is still intact.

Of course, in a sleeve having a circumferential perforation, the indication of seal breakage is also of the utmost importance. Therefore, the perforation of the sleeve shrunk around the syringe is preferably not present at the junction between the needle connection and the needle guard. Rather, the perforation is preferably present in the area where the needle guard adjoins the needle connection, at a position a short distance from the open end of the guard. This distance between the perforation and the end of the needle guard is not critical and, dependent on the length of the sleeve of shrinkable sheet, usually is between 1 and 10 mm. If this distance is larger, the fragment of the sleeve remaining on the needle connection or the front end of the barrel may form an obstruction when administering an injection. When using a needle mount as the needle connection, as described in the above-mentioned Netherlands Patent Applications Nos. 7401607 and 7603511, a sleeve of shrinkable sheet having a length of approximately 2 cm is preferably used and is shrunk around the syringe in such manner that the perforation is present at a point approximately 2 mm from the end of the needle guard. When the needle guard has been removed, it has now become substantially impossible to return it to its original location because the broken portion of the sleeve, which has remained on the needle mount, prevents the reconnection of the needle guard to the needle mount.

When the syringe according to the invention is used, the needle guard should be removed by rotating it relative to the barrel and then exerting a force directed away from the barrel on the needle guard. In the first movement, the rotating movement, the seal must also be broken. It will be obvious that the force which is necessary to detach the needle guard from the needle connection or the front end of the barrel is increased by the seal. When the user of the syringe has to apply too large a force to remove the needle guard, the possibility exits that the needle will be bent or broken. It is therefore important for the breaking of the perforation to take place without much effort. it has been found that the seal, when the sealing member used is a sleeve having a circumferential perforation, can be easily broken when the degree of perforation of the circumferential perforation in the sleeve of shrinkable sheet is at least 50%, preferably 60–75%.

Of course the invention also relates to a prefilled syringe, i.e. a syringe in which the barrel is filled with an injection liquid, which is locked in a sealing manner by the piston at the rear side of the barrel.

The invention also relates to a multi-chamber syringe, wherein more than one injection liquid are or can be stored separately from each other, e.g., by stoppers.

BRIEF DESCRIPTION OF THE DRAWINGS

The invention will now be described in greater detail with reference to the drawings. In the drawings, FIG. 1 is a longitudinal sectional view of an embodiment of a syringe according to the invention prior to use of the syringe;

FIG. 2 shows the essential part of the longitudinal sectional view of the syringe shown in FIG. 1;

FIG. 3 is a longitudinal sectional view of the same part of the syringe as shown in FIG. 2, but while the needle guard is removed; and FIG. 4 is a longitudinal sectional view of another embodiment of a syringe according to the invention.

DETAILED DESCRIPTION OF THE PREFERRED EMBODIMENTS

Reference numeral 11 in FIG. 1 denotes a glass barrel which communicates with an injection needle 12. A breakable seal, not visible in the drawing, in the form of a diaphragm or a stopper is present between the barrel and the cannula. The injection needle is connected to the barrel by means of a needle mount 14. The needle is surrounded by a needle guard 13 which is connected to the neck of the needle mount by means of the thickened open end 23. The injection liquid present in the barrel is bounded on the lower side by a piston 15 which can be moved by a piston rod 16. The barrel furthermore comprises on its outside a finger grip 17. As is also shown in FIG. 2, a sleeve 18 of PVC shrinkable sheet having a perforation 19 is shrunk around the needle mount and around the thickened open end of the needle guard. Said perforation is present at the area of the thickened part the of needle guard, at a point approximately 2 mm in distance from the open end 21 of the needle guard.

FIG. 3 shows the syringe during the instant at which the needle guard is removed to enable use of the syringe. At that instant during which the rotating movement of the needle guard relative to the barrel has already taken place and the perforation has then also been broken, the needle guard is removed from the injection needle. It will be obvious from FIG. 3 that it has now become substantially impossible to place the needle guard back to its original position because the broken portion 20 of the sleeve prevents this return.

In the embodiment shown in FIG. 4 the sleeve 22 of PVC shrinkable sheet has an elongated portion remote from the injection needle, that is shrunk around the main part of the barrel is. Thus the barrel almost completely, apart from the fingergrip connection, tightly enwrapped by the sleeve, so that the sleeve also serves as a protection against breakage of the glass barrel.

We claim:

1. A disposable hypodermic syringe designed to allow a user of the syringe to easily and accurately determine if the sterility of the syringe has been compromised, said syringe including:
   a barrel having a front open end and a rear open end, said barrel being adapted to receive a piston that is movable in the barrel and seals same, said piston being adapted for connection to a piston rod inserted through the rear open end of the barrel;
   a needle mount provided at the front open end of the barrel, said needle mount having a narrowed sleeve-like portion at an end remote from the barrel, said sleeve-like portion having an injection needle connected thereto;
   a needle guard having a thickened open end that is detachably connected to the sleeve-like portion of the needle mount in a functionally clamping manner, thereby achieving a sterile sealing of the needle; and
   a sealing member adapted to seal the connection between the needle mount and the needle guard in a manner such that breakage of the seal is easily and accurately detectable by a user of the syringe, said sealing member comprising a sleeve of shrinkable plastic sheet disposed around the connection between the needle mount and the needle guard in a manner such that reconnection of the needle guard to the needle mount after initial removal of the needle guard is substantially prevented, said sleeve having a first end shrunk around the needle guard and a second end shrunk around the needle mount and optionally also around the barrel of the syringe.

2. The syringe of claim 1, wherein the sleeve is unperforated and is shrunk around the front portion of the syringe so that the second end of the sleeve forms a radially inwardly directed collar behind a thickened portion of the needle mount, and so that the first end of the sleeve forms a cylinder having a diameter which remains the same throughout the area where the needle guard is connected to the needle mount.

3. The syringe of claim 1, wherein the sleeve includes a circumferential perforation, said perforation being located around a portion of the needle guard adjoining the needle mount at a point a short distance from the thickened open end of the needle guard.

4. The syringe of claim 3, wherein the degree of perforation in the circumferential perforation of the sleeve is at least 50 percent .

5. The syringe of claim 4, wherein the degree of perforation is 60 to 75 percent.

6. The syringe of claim 1, wherein the barrel is filled with one or more injection liquids, the barrel being closed in a sealing manner by the piston at the rear end of the syringe.

7. The syringe of claim 3, wherein the sealing member consists essentially of a sleeve of a shrinkable plastic sheet.

* * * * *